United States Patent [19]

Crissman et al.

[11] Patent Number: 5,418,169
[45] Date of Patent: May 23, 1995

[54] CHROMOSOME CHARACTERIZATION USING SINGLE FLUORESCENT DYE

[75] Inventors: Harry A. Crissman, Los Alamos, N. Mex.; Gregory T. Hirons, Irvine, Calif.

[73] Assignee: The Regents of the University of California, Office of Technology Transfer, Alameda, Calif.

[21] Appl. No.: 218,090

[22] Filed: Mar. 25, 1994

[51] Int. Cl.⁶ ........................................... G01N 21/64
[52] U.S. Cl. ..................... 436/94; 436/172; 436/800; 435/6; 209/577; 209/578; 250/461.2; 935/19; 935/77
[58] Field of Search ............... 436/518, 519, 63, 94, 436/172, 800, 824; 435/1, 6; 250/461.2, 459.1; 209/3.1, 576, 577, 578

[56] References Cited

PUBLICATIONS

Hirons, G. T., and Crissman, H. A. *Evaluation of two new fluorochromes, TOTO and YOYO, for DNA content analysis in cells and chromosomes by flow cytometry.* 16 Congress of the International Society for Analytical Cytology. 21–26 Mar. 1993. Colorado Springs, Colo. 1993.

Hays S. Rye et al., "Fluorometric Assay Using Dimeric Dyes For Double-and Single-Stranded DNA and RNA With Picogram Sensitivity," Analytical Biochemistry 208, pp. 144–150 (1993).

J. W. Gray et al., "High-Speed Chromosome Sorting," Science, 23:323 (1987).

*Primary Examiner*—David A. Redding
*Attorney, Agent, or Firm*—Ray G. Wilson

[57] ABSTRACT

Chromosomes are characterized by fluorescent emissions from a single fluorescent dye that is excited over two different wavelengths. A mixture containing chromosomes is stained with a single dye selected from the group consisting of TOTO and YOYO and the stained chromosomes are placed in a flow cytometer. The fluorescent dye is excited sequentially by a first light having a wavelength in the ultraviolet range to excite the TOTO or YOYO to fluoresce at a first intensity and by a second light having a wavelength effective to excite the TOTO or YOYO dye to fluoresce at a second intensity. Specific chromosomes may be identified and sorted by intensity relationships between the first and second fluorescence emissions.

2 Claims, 3 Drawing Sheets

CHROMOSOME CHARACTERIZATION USING SINGLE FLUORESCENT DYE

BACKGROUND OF THE INVENTION

This invention is related to the characterization of individual chromosomes and, more particularly, to the characterization of individual chromosomes for separation using flow cytometry. This invention was made with government support under Contract No. W-7405-ENG-36 awarded by the U.S. Department of Energy. The government has certain rights in the invention.

The entire set of human chromosomes, 22 autosomes plus the X and Y chromosomes, contains all of the nuclear DNA in human cells, i.e., the human genome. Separating the chromosomes contained in a cell sample provides a convenient way to make chromosome libraries, each of which is a subset of the genome. One convenient separating technique is flow cytometry, or flow sorting, of the chromosomes.

Chromosome sorting by flow cytometry requires that a chromosome or chromosomes to be separated have some identifiable characteristic that can be identified for use in the sorting process. Such chromosome sorting conventionally requires staining a chromosome or chromosomes with two different fluorescent dyes. A typical process is described in J. W. Gray et al., "High-Speed Chromosome Sorting," 23 Science 323–329 (Oct. 1987). A liquid suspension of the chromosomes is stained with two fluorescent dyes, e.g., Hoechst 33258, which binds preferentially to AT-rich DNA, and chromomycin $A_3$ (CA3), which binds preferentially to GC-rich DNA. The stained chromosomes pass through two laser beams, one beam to excite each dye to fluorescence. A combination of the fluorescent emission intensities from the two dyes allows many of the chromosomes to be uniquely characterized for separation from other chromosomes, as is fully shown by FIG. 1 herein.

FIG. 1 depicts a conventional bivariate profile for human GM130 chromosomes stained with Hoechst 33258 and $CA_3$. The combination of fluorescent intensities allows the chromosomes to be karyotyped for separating the chromosomes by flow cytometry, as described by Gray. However, two staining processes must be used for the conventional technique. Further, conventional stains have relatively low quantum efficiencies so that correspondingly high power output lasers are required to obtain sensitive results.

Accordingly, it is an object of the present invention to provide for chromosome karyotyping using only a single fluorescent dye.

Another object of the present invention is to provide sensitive fluorescence signals with relatively low power lasers.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method of this invention may comprise the application of a single fluorescent dye to separate selected chromosomes from a mixture. The mixture is stained with a single dye selected from the group consisting of TOTO and YOYO and the stained chromosomes are placed in a flow cytometer. The fluorescent dye is excited sequentially by a first light having a wavelength in the ultraviolet (uv) range to excite the TOTO or YOYO dye to fluoresce at a first intensity and by a second light having a wavelength effective to excite the TOTO or YOYO dye to fluoresce at a second intensity. Specific chromosomes are identified by intensity relationships between the first and second fluorescence emissions.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE DRAWINGS

Figure 1:
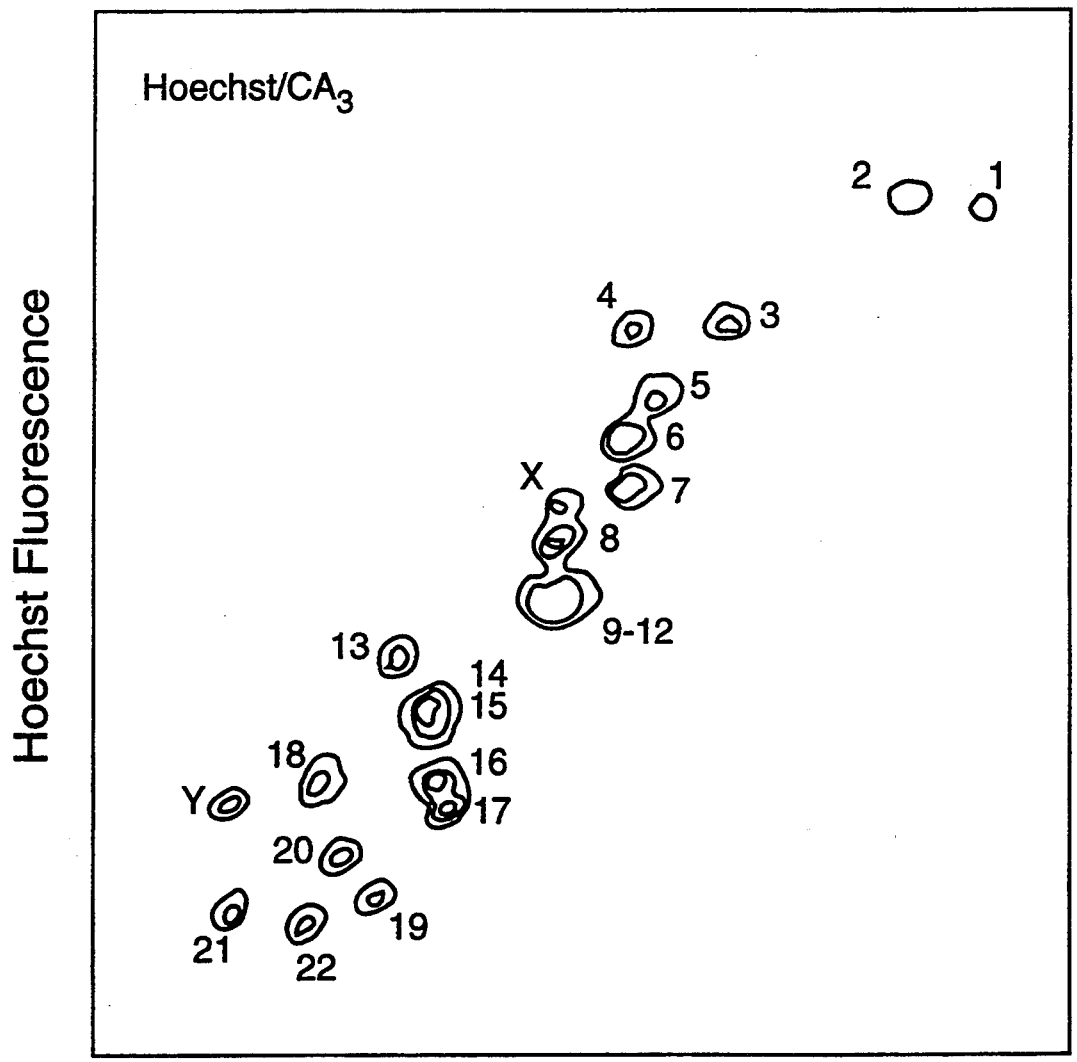
FIG. 1 conventionally depicts a bivariate profile for human GM130 chromosomes with fluorescence intensities from Hoechst and $CA_3$ plotted against each other for a mixture of chromosomes to illustrate the separation of chromosomes that may be available for two-dye staining.

Flow cytometric studies on human chromosomes have been performed using new cyanine dyes: TOTO (a dimer of thiazole orange) and YOYO (a dimer of oxazole yellow). TOTO and YOYO have high quantum efficiencies (QEs), i.e., fluorescence yield for each exciting photon, and emit at wavelengths of 530 nm and 510 nm, respectively, when excited at 488 nm and 457 nm, which are exciting wavelengths that are conventionally used in flow cytometers (FCMs). TOTO and YOYO also emit at the wavelengths of 530 nm and 510 nm when they are excited by laser light having a wavelength range in the uv region of 300–360 nm, although the emissions have only about one tenth the intensity of emissions from the 488/457 nm excitations. Surprisingly, bivariate analyses of human chromosomes stained with TOTO or YOYO alone and excited sequentially with uv and visible wavelengths showed resolution of many individual chromosome peaks so that sorting of selected chromosomes could be done using only a chromosome mixture stained with TOTO or YOYO. As used herein, sequential excitation means that the stained cells are excited by a first laser, the first fluorescence emissions are detected, excited by a second laser, and the second fluorescence emissions are detected.

TOTO and YOYO dyes are commercially available as TOTO-1 and YOYO-1 from Molecular Probes Inc., Eugene, Oregon, and are the dyes used in the examples herein. The TOTO and YOYO dyes have QEs on the order of 1100 and 3200, respectively, when bound to double-stranded DNA, compared to a QE of about 35 for ethidium homodimer and less than one for conventional ethidium bromide. The ultrasensitivities of TOTO and YOYO, along with their characteristic excitation wavelengths of 488 and 457 nm, respectively, have been used in the present invention to provide a single dye bivariate analysis.

PROTOCOL

Cell and Culture Conditions.

Human lymphoblast GM130 cells, used for chromosome isolation, were grown routinely at 37° C. in suspension culture in T150 tissue culture flasks containing RPM1 1640 medium (Gibco BRL, Grand Island, N.Y.) supplemented with 10% FBS, penicillin, streptomycin, and 1% of 200 mM L-flutamine (Gibco BRL, Grand Island, N.Y.) at densities ranging from $0.6$–$1.2 \times 10^6$ cells/mi. At a density of $\sim 0.9 \times 10^6$ cells/ml, cells were blocked in mitosis by treatment with 0.11 μg/ml Colcemid (Gibco BRL, Grand Island, N.Y.) for $\sim 15.5$ hour prior to chromosome isolation.

GM130 Metaphase Chromosome Polyamine Isolation and Staining.

The procedure is generally described in L. S. Cram et al, "Polyamine Buffer for Bivariate Human Flow Cytogenetic Analysis and Sorting," 33 Flow Cytometry, pp. 377–382, Z. Darzynkiewicz and H. A. Crissman. (eds), Academic Press Inc., New York (1984), with the following modifications. To samples containing $\sim 7$–$8 \times 10^6$ miotic cells, 5.0 ml of Ohnuki's hypotonic swelling solution was added for $\sim 70$ minutes. The samples were vortexed for $\sim 30$ seconds to rupture the swelled mitotic GM130 cells.

Prior to staining, chromosome samples were mildly vortexed a few seconds and centrifuged at room temperature for 3 minutes at 30 g. The supernatants containing the chromosomes were then pipetted into small Eppendorf tubes. The samples were then stained directly with stock solutions of TOTO or YOYO at least 18 hours prior to FCM analysis to yield final dye concentrations of $5.0 \times 10^{-6}$ M for TOTO and $10^{-5}$ M for YOYO. These concentrations were chosen from experiments employing dye concentrations ranging from $10^{-6}$ to $10^{-5}$ M. Immediately prior to FCM analysis, the samples were mildly vortexed a few seconds and centrifuged at room temperature for 15 second intervals at speeds of 30 g, 140 g, 280 g, 140 g, and 30 g again without stops between each time interval. The supernatants containing the chromosomes were then filtered through a 60 micron nylon filter and placed on ice until FCM analysis.

Flow Cytometric Analyses.

GM130 chromosomes were analyzed with an EPICS 752 dual beam flow cytometer (Coulter Cytometry, Hialeah, Florida) equipped with two Innova 90—5 argon ion lasers (Coherent, Palo Alto, Calif.). Chromosome samples stained with TOTO alone and YOYO alone were analyzed with sequential uv and 488 nm excitation and with sequential uv and 457 nm excitation, respectively. Long pass barrier filters of 515 and 495 nm were used for 488 and 457 nm excitations, respectively. In addition, a 418 nm uv-blocking filter was used for all samples to filter out the laser excitation light and eliminate light scattering signals from chromosomes that would interfere with the fluorescence analysis. The output power of the 488 nm excitation was 925 mW, 145 mW for the 457 nm excitation and 135 mW for the uv excitation. The fluorescence emission maxima for the dimers TOTO and YOYO bound to dsDNA are $\sim 530$ and 510 nm, respectively, for excitation in both wavelength ranges (488/457 nm and uv in the 300–360 nm range).

Human GM130 Chromosome Resolution Using TOTO and YOYO Fluorochromes.

Figure 2:
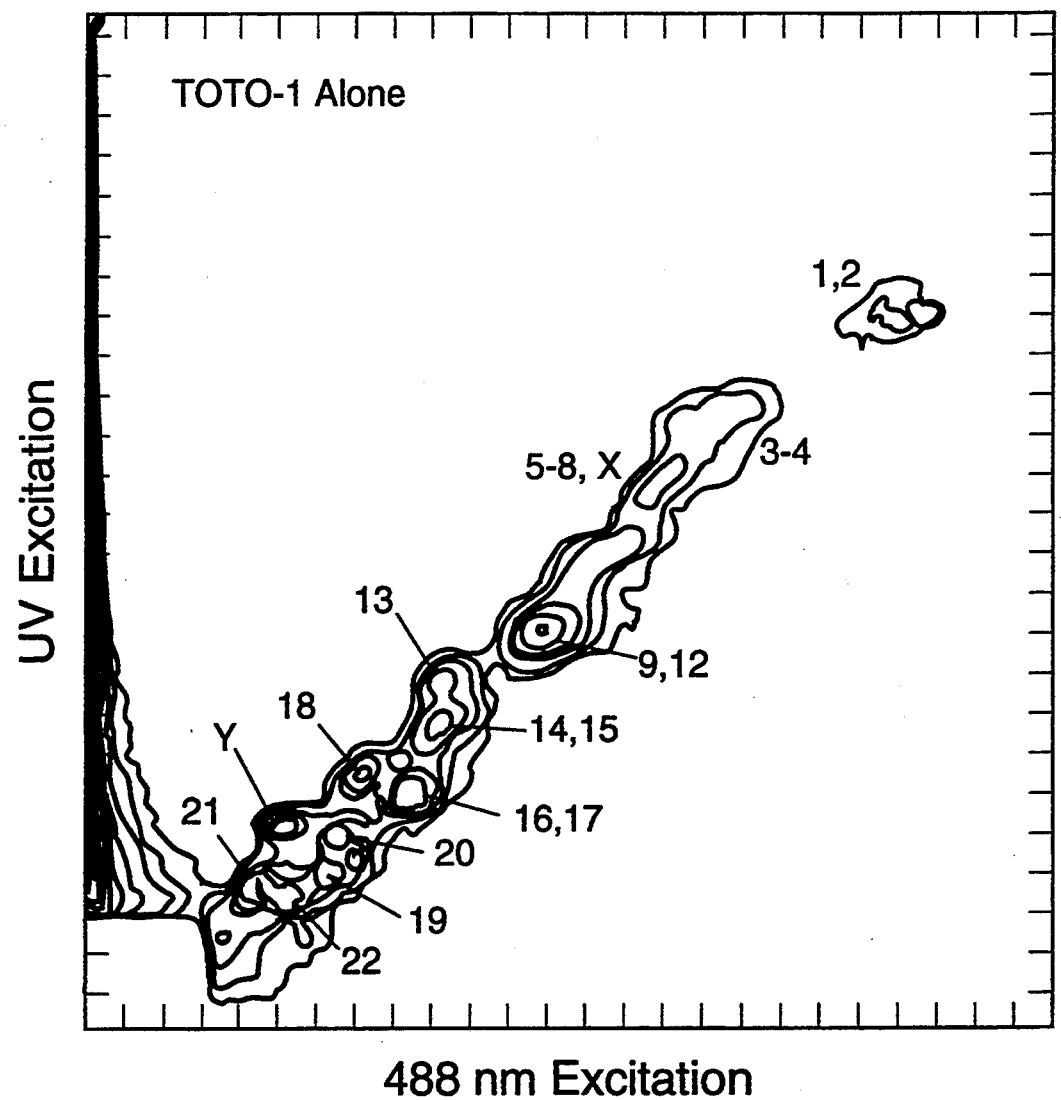
FIG. 2 depicts a bivariate profile for GM130 chromosomes stained with TOTO-1 alone.
Figure 3:
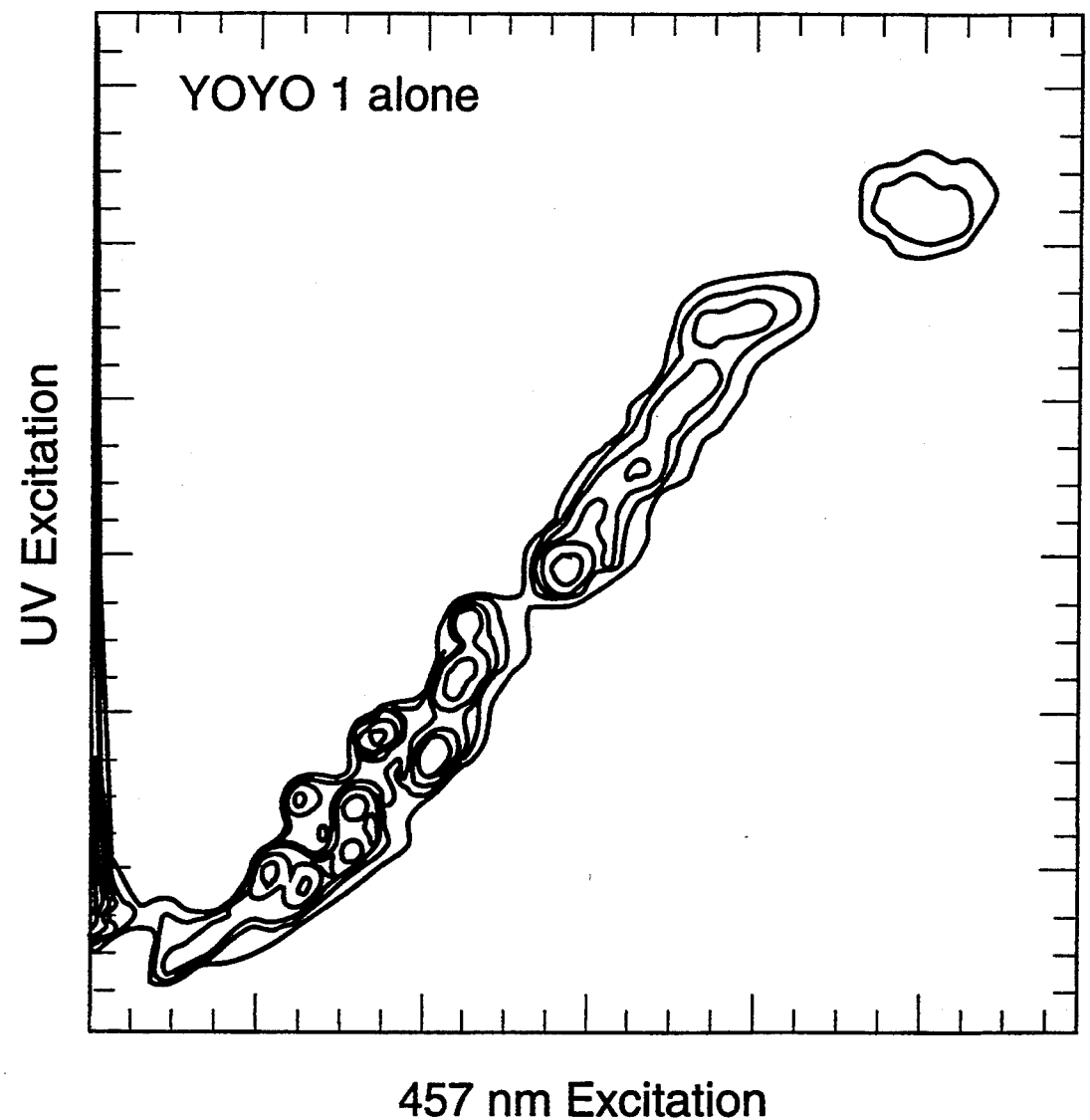
FIG. 3 depicts a bivariate profile for GM130 chromosomes stained with YOYO-1 along with autosome and chromosome assignments.

The FCM bivariate distributions for human lymphoblast GM130 chromosomes stained with TOTO alone and with YOYO alone are shown in FIGS. 2 and 3, respectively. In accordance with this invention, the bivariate profiles, obtained from sequential uv and visible excitation of TOTO- or YOYO-stained chromosomes, resolved peaks corresponding to many individual chromosomes. The assignment of chromosome peaks in FIG. 2, for the sample stained with TOTO only and excited sequentially with 488 nm and uv lasers, correspond to the 22 autosomes and both sex chromosomes in human GM130 cells. These chromosome assignment are based on results from GM130 chromosomes stained with Hoechst 33258 and chromomycin (CA3), as shown in FIG. 1. It should be noted that the resolution of the smaller chromosomes shown in FIGS. 2 and 3 for TOTO and YOYO, particularly chromosomes 9–22 and chromosome Y, is comparable to that of the Hoechst/CA3 sample in FIG. 1.

Thus, when compared to the Hoechst/CA3 chromosome data, either TOTO or YOYO alone can at least partially resolve many of the human GM130 22 autosomes and 2 sex chromosomes using sequential UV and visible excitation. These results are surprising since spectrofluoremetric studies showed no differences in fluorescence emission profiles of cyanine-stained DNA samples excited with either uv or visible wavelengths. In addition, FCM bivariate analyses of YOYO-stained nuclei gave no indication of differences in cyanine-dye binding, since the fluorescence emission patterns were nearly identical for excitation with uv or 457 nm. Bivariate results obtained with cyanine -stained chromosomes could be attributed to photobleaching of the cyanine dyes when chromosomes pass first through the uv laser beam and this is still under investigation. In any event, the ability to obtain significant chromosome resolution from staining with only one dye may also indicate complex differences in binding and/or fluorescence properties related to uv and visible excitation of TOTO and YOYO when bound to different chromosomes.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for characterizing selected chromosomes in a solution, comprising:
   staining said chromosomes with a single dye selected from the group consisting of TOTO and YOYO;
   placing said chromosomes stained with said dye in a flow cytometer;
   exciting said dye sequentially with a first light having a wavelength in the ultraviolet range to excite said TOTO or said YOYO dye to fluoresce at a first intensity and a second light having a wavelength in the visible range effective to excite said YOYO dye or said TOTO dye to fluoresce at a second intensity; and characterizing specific chromosomes having known relationships between said first and second fluorescence intensities.

2. A method according to claim 1, wherein said second light has a wavelength of about 488 nm for exciting TOTO and about 457 nm for exciting YOYO.

* * * * *